(12) United States Patent
Nouchi et al.

(10) Patent No.: US 7,883,844 B2
(45) Date of Patent: Feb. 8, 2011

(54) METHOD FOR PROPAGATING INFLUENZA VIRUS

(75) Inventors: Toshinobu Nouchi, Kumamoto-ken (JP); Kiyoto Nishiyama, Kumamoto-ken (JP); Keishin Sugawara, Kumamoto-ken (JP)

(73) Assignee: Juridical Foundation the Chemosero-Therapeutic Research Institute, Kumamoto-Ken (JP)

( * ) Notice: Subject to any disclaimer, the term of this patent is extended or adjusted under 35 U.S.C. 154(b) by 143 days.

(21) Appl. No.: 12/300,625

(22) PCT Filed: May 11, 2007

(86) PCT No.: PCT/JP2007/059730

§ 371 (c)(1), (2), (4) Date: Nov. 12, 2008

(87) PCT Pub. No.: WO2007/132763

PCT Pub. Date: Nov. 22, 2007

(65) Prior Publication Data

US 2009/0181446 A1    Jul. 16, 2009

(30) Foreign Application Priority Data

May 11, 2006   (JP)   .............................. 2006-132049

(51) Int. Cl.
  *C12Q 1/70* (2006.01)
(52) U.S. Cl. ......................................................... 435/5
(58) Field of Classification Search ........................ None
  See application file for complete search history.

(56) References Cited

U.S. PATENT DOCUMENTS

| 4,500,513 | A  | * | 2/1985  | Brown et al. ............. 424/209.1 |
| 6,656,720 | B2 | * | 12/2003 | Groner et al. ............. 435/235.1 |
| 2003/0044962 | A1 | | 3/2003 | Makizumi et al. |

FOREIGN PATENT DOCUMENTS

| JP | 153723 | 11/1980 |
| JP | 201574 | 9/1987 |
| JP | 509081 | 8/1999 |
| JP | 507825 | 6/2000 |
| WO | 96/15232 A1 | 5/1996 |
| WO | 97/37000 A1 | 10/1997 |
| WO | 97/37001 A1 | 10/1997 |
| WO | 0164846 A1 | 9/2001 |
| WO | 2005/026333 A1 | 3/2005 |
| WO | 2006/051946 A1 | 5/2006 |

OTHER PUBLICATIONS

Genzel et al, Vaccine, 2006, vol. 24, pp. 3261-3272.*
Orstavik., "Susceptibility of Continuous Lines of Monkey Kidney Cells to Influenza and Parainfluenza Viruses in the presence of trypsin" Acta path. microbiol. scand. Sect. B, 89: 179-183 (1981).
Kido et al., "Pulmonary surfactant is a potential endogenous inhibitor of proteolytic activation of Sendai virus and influenza A virus" Federation of European Biochemical Societies, vol. 322(2):115-119 (1993).
Yamaoka et al., "MDCK cell cultures supplemented with high concentrations of trypsin exhibit remarkable susceptibility to influenza C virus" Arch Virol,140:937-944 (1995).
Merten et al., Production of influenza virus cell cultures for vaccine preparation, Advances in Experimental Medicine and Biology, 397:141-151 (1996).
Merten et al., Production of influenza virus in serum-free mammalian cell cultures, Developements in Biological Standardization, 98:23-37 (1997).
Merten et al., The new medium MDSS2N, free of any animal protein supports cell growth and product of various viruses, Cytotechnology, 30(1-3):191-201 (1999).
Kessler et al., Suitability of MDCK cells grown in a serum-free medium for influenza virus protection, Developements in Biological Standardization, 98:13-21 (1999).
Mancini et al., Avaliacao DA tripsina na multiplicacao devirus influenza em culturas MDCK, Revista de Farmacia E Bioquimica Da Universidade De Sao Paulo, 29(2):89-95 (1993).

* cited by examiner

*Primary Examiner*—Ali R. Salimi
(74) *Attorney, Agent, or Firm*—Browdy and Neimark, PLLC

(57) ABSTRACT

A method for producing influenza virus on large scale is provided. A method for propagating influenza virus which comprises, after removing or decreasing a trypsin inhibitor secreted into culture of MDCK cells (cell line derived from dog kidney) by washing with a culture medium or a buffer, inoculating influenza virus into said cells and culturing said influenza virus-inoculated cells in a culture medium supplemented with trypsin.

5 Claims, 2 Drawing Sheets

METHOD FOR PROPAGATING INFLUENZA VIRUS

TECHNICAL FIELD

The present invention relates to a method for propagating influenza virus in tissue culture. More particularly, the present invention relates to a method for propagating influenza virus characterized in that, after a trypsin inhibitor secreted into culture of MDCK cells (cell line derived from dog kidney) is removed or decreased by washing with a culture medium or a buffer, influenza virus is inoculated into said cells and said influenza virus-inoculated cells are cultured at a high cell density in a culture medium containing a high concentration of trypsin.

BACKGROUND ART

Influenza virus is a polymorphic RNA virus of Orthomyxoviridae with a diameter of about one ten thousandth millimeters (100 nm). When this virus infected human, symptoms are observed such as fever of more than 38° C., headache, arthralgia, muscular pain, and also pharyngeal pain, snivel, cough, etc. Influenza virus may adsorb to sialic acid in epidermal cells present within the nasal cavity or on the surface of the pharyngeal mucosa and be taken into cells by endocytosis, followed by release of ribonucleoprotein (RNP) into cells through membrane fusion. RNP is then transferred to the cellular nucleus where each component of the virus is synthesized using the cellular transcription/translation system and viral particles are then formed on the cellular surface using the lipid membrane from the cell. The viral particles are cut off from the cellular surface by the action of viral neuraminidase and released out of the cell.

Influenza virus is divided into three types A, B and C, among which types A and B spread epidemically. On the surface of the types A and B influenza viral particles are glycoproteins, i.e. hemagglutinin (HA) and neuraminidase (NA), which are a target antigen for protective immunization of infection. In case of type A influenza virus, in particular, there exist antigenically different subtypes, i.e. 15 subtypes for HA and 9 subtypes for NA, and viruses with various combinations of these subtypes spread widely not only in human but also in other hosts such as pig or chicken. Therefore, viruses of animal-derived subtype may invade human as zoonosis.

For influenza virus, the virus acquires infectivity through cleavage of hemagglutinin (HA) on the surface of the viral particles into HA1+HA2 and infection proceeds in multiple steps. This HA cleavage occurs through the action of a trypsin-like protease secreted from the target organs, the intestine or the airway, in case of chicken. Thus, infection in the organs may proceed through the HA cleavage and activation to exhibit pathogenicity. Also, Kido et al., from the study of mechanism of influenza viral infection, showed that cleavage and activation of the HA antigen on the viral surface by a protease (tryptase Clara) derived from the host is important for the establishment of infection (see, for instance, Non-patent reference 1).

Current influenza vaccines are either a split vaccine, which is prepared by inoculating influenza virus for the preparation of a vaccine into the allantoic cavity of growing chicken eggs for culture and propagation of the virus, concentrating and purifying the virus from the chorio-allantoic liquid by centrifugation, and treating the viral particles with ether or a surfactant to remove most of lipid components thought to be a cause of adverse side effects so as to obtain a suspension of HA fractions, followed by inactivation (removal of pathogenicity) with formalin; or a subunit vaccine prepared by disintegration of viral particles with a surfactant and further purification. Thus, since influenza vaccine is made from a fertilized egg and hence hasty mass production is not possible, its expected amount of production is prudently determined taking into consideration various conditions every year.

For a method of propagation of virus by tissue culture, a method is reported wherein human influenza viruses are cultured in Vero cells in the presence of trypsin in the culture medium at a minimum concentration of about 0.05 µg/ml (preferably about 0.05 µg/ml and about 0.5 µg/ml) throughout the viral growth cycle (see, for instance, Patent reference 1). However, this method is one for effectively isolating influenza virus from animals infected with said virus and the reference does not disclose a method suitable for the preparation of a vaccine.

Patent reference 1: Japanese patent publication No. 506081/1999

Non-patent reference 1: FEBS LETTERS, 322, p 115-119 (1993)

DISCLOSURE OF THE INVENTION

Technical Problem to be Solved by the Invention

As described above, a method for preparing influenza viruses using a growing chicken egg is problematic from viewpoint of safety. Alternative method for preparing viruses includes one by tissue culture but it can hardly be said that a method has been developed that may provide a sufficient amount of viruses for the production of a vaccine.

Accordingly, a purpose of the present invention is to provide a novel method for propagating viruses to ensure a sufficient amount of viruses for use as vaccine material.

Means for Solving the Problems

Under the circumstances, the present inventors have continued research assiduously so as to attain the purpose described above and as a consequence have found that a substance having a trypsin inhibitor activity is secreted into culture of MDCK cells (Japanese Patent Applications No. 2004-329966 and No. 2005-184500) and that production of influenza viruses could be increased by washing MDCK cells with a culture medium or a suitable buffer to remove or decrease the trypsin inhibitor secreted into culture before inoculation of influenza viruses into MDCK cells. Furthermore, the present inventors have found that the addition of a concentration of trypsin to the culture of influenza virus-infected cells could enhance the effect to thereby complete the present invention.

Thus, the present invention provides a method for propagating influenza virus as follows:

1. A method for propagating influenza virus which comprises, after removing or decreasing a trypsin inhibitor secreted into culture of influenza virus-sensitive cells by washing with a culture medium or a buffer, inoculating influenza virus into said cells and culturing said influenza virus-inoculated cells.

2. A method of 1 wherein influenza virus-inoculated cells are cultured in a culture medium containing trypsin at 0.45 to 2.7 U/mL.

3. A method of 1 wherein said method comprises steps (1) to (5) as follows:

(1) subjecting cell culture to centrifugation at a low speed or membrane filtration to isolate cells from culture supernatant;

(2) washing the cells with a culture medium or a buffer;

(3) inoculating influenza virus into the cells;

(4) culturing the influenza virus-inoculated cells; and (5) adding a trypsin solution at a final concentration of trypsin of 0.45 to 2.7 U/mL while culture of said influenza virus-inoculated cells.

4. A method of any one of 1 to 3 wherein m.o.i. of influenza virus is 0.0001 to 0.01 and a cell density of said influenza virus-inoculated cells is $3\text{-}11\times10^6$ cells/mL.

5. A method of any one of 1 to 4 wherein the influenza virus-sensitive cells are selected from the group consisting of MDCK cells (cell line derived from dog kidney), Vero cells (cell line derived from African green monkey kidney), EBx cells (cell line derived from chicken embryonic stem cell), PER.C6 cells (cell line derived from human retinal cells) and SK-NEP-1 cells (cell line derived from human kidney).

6. A method of any one of 1 to 5 wherein said influenza virus-inoculated cells are cultured in suspension culture.

More Efficacious Effects Than Prior Art

In accordance with the present invention, a method for producing a large amount of influenza virus is provided. Before inoculating influenza virus into influenza virus-sensitive cells, said cells are washed with a culture medium or a suitable buffer. By this, a trypsin inhibitor that inhibits propagation of influenza virus is removed or decreased, a rate of culture exchange being 50% or more, to allow for production of a large amount of influenza virus in the culture medium. By adding a high concentration of trypsin, at 0.45 to 2.7 U/mL, while culture of influenza virus-inoculated cells, production of influenza virus may further be increased. Preferably, a high cell density at $3\text{-}11\times10^6$ cells/mL is used. By this, both viral productions per culture solution and per cell number may be increased to thereby decrease an amount of a viral solution when purified.

BEST MODE FOR CARRYING OUT THE INVENTION

Figure 1:
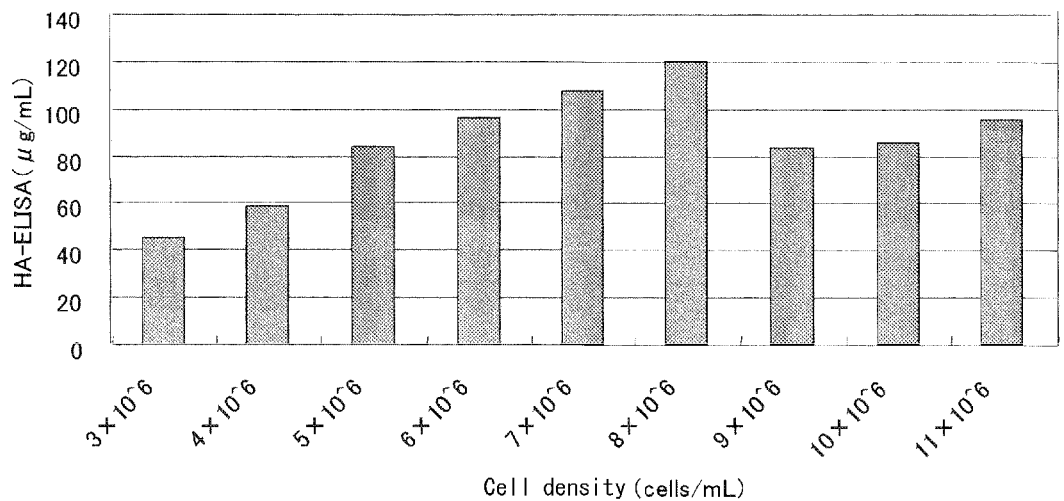
FIG. 1 is a graph showing a viral amount in a culture medium when a variety of initial cell densities are used in viral production by tissue culture.

The present invention features a method for propagating influenza virus which comprises, after washing influenza virus-sensitive cells with a culture medium or a buffer, inoculating influenza virus into said cells and culturing said influenza virus-inoculated cells, and optionally adding a high concentration of trypsin when the influenza virus-inoculated cells are cultured.

Cells for use in the present invention may be any that are sensitive to influenza virus. Such cells include, for instance, MDCK cells (cell line derived from dog kidney), Vero cells (cell line derived from African green monkey kidney), EBx cells (cell line derived from chicken embryonic stem cell), PER.C6 cells (cell line derived from human retinal cells) and SK-NEP-1 cells (cell line derived from human kidney). These cells have been registered with ATCC (American Type Culture Collection) as CCL-34, CCL-81 and HTB-48, respectively, and may be purchased.

A culture medium may be one ordinarily used for cell culture and includes, for instance, M202 (JRH Bioscience, article to special order), T7m (JRH Bioscience, article to special order), EX-CELL293 (JRH Bioscience, 14570), EX-CELL MDCK (JRH Bioscience, 14580), M199-earle base (Nissui), Eagle MEM (E-MEM; Nissui), Dulbecco MEM (D-MEM; Nissui), SC-UCM102 (Nissui), UP-SFM (GIBCO BRL), EX-CELL302 (Nichirei Corporation), EX-CELL293-S (Nichirei Corporation), TFBM-01 (Nichirei Corporation), ASF104 (Ajinomoto) and the like, and any of these may be used. When cells are propagated, a culture medium supplemented with an amino acid, a salt, an anti-fungal or anti-bacterial agent, or for enhancing propagation of cells, a culture medium supplemented with a hydrolysate derived from plant are sometimes used. However, when a cell culture is recovered and purified, a culture medium containing no additives is to be used. In this context, "cell culture" refers to a mixture of cells cultured by tissue culture and a culture medium. For use as an influenza vaccine material, it is preferable that none of said hydrolysate is added throughout the steps of the method. pH of a culture medium may be adjusted to 6.5 to 8, preferably 6.8 to 7.3, as suited for propagation of animal cells with a suitable buffer, e.g. sodium hydrogen carbonate, HEPES.

Cell culture includes a standing culture in which cells are attached at the bottom of a fermenter and a suspension culture in which cells are cultured while suspended in a culture medium. For cell culture at a level of industrial production, a suspension culture is preferable. A suspension culture may be carried out either by attaching cells to a carrier such as a microcarrier and suspending said carrier or by directly suspending cells without a carrier. Preferably, MDCK cells adapted to suspension culture without need of a microcarrier (hereinafter also referred to as "MDCK cells adapted to suspension culture") are used. For use of a microcarrier, various microbeads of different types in size, shape, density, surface electric charge and surface coating material that are commercially available may appropriately be selected. For instance, microbeads include Cytodex, Biosilon (Nalge Nunc International, K.K.) and CELLYARD (Pentax), preferably Cytodex (Cytodex I, Amersham Bioscience). Said Cytodex may be used at 1 to 10 g, preferably 3 to 5 g, per 1 L of culture.

Before inoculating the virus into MDCK cells adapted to suspension culture, the cells are washed with a fresh culture medium or a suitable buffer such as e.g. PBS or Tris buffer, preferably with a fresh culture medium. This replaces a culture medium used for cell culture with a fresh culture medium. A rate of culture exchange by washing the cells is 50% or more, preferably 75% or more, more preferably 100%. Specifically, MDCK cells cultured and propagated in a spinner flask are subjected to centrifugation at a low speed or membrane filtration to separate cells from culture supernatant. Culture exchange may be carried out such that a fresh culture medium is added to a precipitate of centrifugation or a concentrate of membrane filtration to suspend the cells. When a rate of culture exchange is low, the procedures are repeated so that 100% of a rate of culture exchange may be achieved (which means that culture exchange with a fresh culture medium is done nearly completely). A solution of influenza virus is then added to the thus obtained cell suspension and culture is performed under fixed conditions. After suspending cells after centrifugation in a small amount of a culture medium, influenza virus may be inoculated into the cells and subsequently a suitable amount of a culture medium may be added thereto. Trypsin is optionally added to a culture medium. It may be present in a culture medium at the beginning of culture or added dropwise while culture.

An initial cell density at the beginning of viral culture may be as high as $3\text{-}11\times10^6$ cells/mL, preferably $3\text{-}8\times10^6$ cells/mL, more preferably $4\text{-}7\times10^6$ cells/mL.

For trypsin, one used for ordinary cell culture may be used, including, for instance, Trypsin 250 (DIFCO), Trypsin (Merk, 108444), Trypsin cGMP (Sigma, T8395), Trypsin (1:250) (GIBCO), derived from pig, or crystalline trypsin (Wako, 207-09891), Trypsin crystal (Kanto Chemical. Co. Inc.) derived from bovine, or genetically recombined Trypzean (Sigma) or rProtease (GIBCO), and the like. Trypsin may be used as a trypsin solution dissolved in water, a buffer or a culture medium. In the present invention, a trypsin solution at a final concentration of 0.45 to 2.7 U/mL, preferably 0.45 to 1.8 U/mL, more preferably 0.45 to 0.9 U/mL, may be used. For influenza virus, A/New Caledonia strain, B/Shandong strain or A/Wyoming strain provided from National Institute of Infectious Diseases may be used. Influenza virus directly isolated from patients infected with the virus may also be used. Isolation of influenza virus may be carried out by replication of the virus at a low multiplicity of infection as disclosed by Webster et al. (Japanese Patent Publication No. 11-509081). Briefly, isolation of influenza virus may be carried out by adding a washing from the throat of patients showing clinical symptoms of influenza to cells and culturing said cells in a culture medium supplemented with about 1% trypsin. In the working examples of the present invention, A/New Caledonia strain and B/Shandong strain are used. Influenza virus for tissue culture may be used at m.o.i of 0.00001 to 0.01, preferably at m.o.i of 0.001 to 0.0001, as used in ordinary viral infection.

Culture conditions may suitably be adjusted depending on a combination of a type of cells, an amount of viral inoculation, scale and method of culture, and the like. For instance, culture temperature may be 32° to 38° C., preferably 33° to 34° C. Duration of culture may be 3 to 5 days, preferably 3 to 4 days. A concentration of carbon dioxide may be 4 to 6%, preferably 5%. A concentration of oxygen may be 2 to 10 ppm, preferably 3 ppm.

A cell density may be measured as ordinary with a hemacytometer. A viral content in a culture medium may be measured either by ELISA (μg/mL) using an antibody to hemagglutinin (HA) of influenza virus or by hemagglutination (fold of dilution) using chicken hemocytes. In the working examples of the present invention, a viral content was determined by ELISA.

For an antibody to HA, a polyclonal antibody and a monoclonal antibody may be used and a desired antibody may suitably be selected in view of sensitivity and specificity. For obtaining a polyclonal antibody, a purified HA as an immunogenic antigen is administered intraperitoneally, subcutaneously, intradermally or intravenously together with a suitable adjuvant such as Freund's complete or incomplete adjuvant as occasion demands and, if necessary, booster immunity is given at an interval of 2 to 4 weeks. After booster immunity, blood is taken and anti-serum is obtained. An animal to be immunized is not particularly limited and animal species capable of producing a desired antibody may be selected from e.g. rat, mouse, rabbit, sheep, horse, chicken, goat, pig, bovine, etc. A polyclonal antibody may be obtained by purifying the obtained anti-serum. Purification of an antibody may be carried out by suitably combining techniques known in the art such as salting-out, ion exchange chromatography, affinity chromatography, and the like.

A monoclonal antibody may be obtained as described below. Namely, antibody-producing cells such as spleen cells or lymphocytes are removed from the immunized animal and fused with myeloma cell strain to prepare hybridomas, in accordance with e.g. Milstein et al., Method Enzymol., 73, 3-46, 1981. Myeloma cell strain such as NSI-Ag4/1 (Eur. J. Immunol., 6:511, 1976), P3X63-Ag8.U1 (Curr. Topics Microbiol. Immunol., 81:1, 1978), X63-Ag8.653 (J. Immunol., 123:1548, 1979), and the like may be used. Hybridomas may be obtained by culture in a HAT medium for a period of time sufficient for non-fused cells to die out, usually from several days to several weeks. From the thus obtained hybridomas, those producing an antibody of interest are then selected and cloned with ordinary limiting dilution using their culture supernatant. Selection of a clone producing an antibody specifically binding to HA may be done with analytical techniques commonly used such as ELISA, RIA, or Western blot. Purification of an antibody may be carried out by suitably combining the above-mentioned known techniques such as salting-out, ion exchange chromatography, affinity chromatography, and the like. An HA-binding antibody may also be prepared by the technique for antibody preparation using phage display (Phage Display of Peptides and Proteins: A Laboratory Manual Edited by Brian K. Kay et al., Antibody Engineering: A PRACTICAL APPROACH Edited by J. McCAFFERTY et al., ANTIBODY ENGINEERING second edition edited by Carl A. K. BORREBAECK).

The anti-HA antibody thus obtained may be incorporated into antigen-antibody assay system (e.g. ELISA) for detecting an HA antigen. For ELISA plate, various commercially available articles may be used. ELISA system for measuring an HA antigen as used in the present invention may be constructed as follows: A solution of an anti-HA antibody, which is antiserum manufactured by applicant diluted by 1000-fold, is put in a 96-well plate (Nunc) and the plate is left to stand at 4-10° C. overnight to let the anti-HA antibody be adsorbed. After removing the solution of the anti-HA antibody, the plate is washed with a suitable washing solution, e.g. a phosphate buffer containing Tween 20, and then coated for non-HA-adsorbed portions with Block Ace or skim milk to prepare an ELISA plate. For measurement of an HA antigen, a culture medium in which influenza virus-infected cells are cultured is put in the above ELISA plate and the plate is left to stand at 37° C. for 1 hour. After washing with the same washing solution as above, an anti-HA rabbit antibody or guinea pig antibody labeled with RI, DIG or fluorescence is added and the plate is further left to stand at 37° C. for 1 hour. After washing with the same washing solution as above, a developing solution, e.g. TMB+Substrate-Chromogen, POD, is added for development, which is measured at a wave length 450 nm. From a calibration curve, an amount of an HA antigen is measured. A sensitivity of this assay system for an HA antigen is 3 ng/mL.

The present invention is explained in more detail by means of the following Examples wherein reagents from Wako Pure Chemical Industries, Ltd. and nacalai tesque are used unless otherwise mentioned.

Example 1

Effect of Trypsin Concentration on High Density Culture of Influenza Virus (1) High Density Culture of A/New Caledonia Strain Dog kidney cells (MDCK) after suspension culture in T7m medium (JRH) were centrifuged at a low speed (2000 rpm×3 min.) and were suspended in 50 mL of fresh T7m medium at an initial cell density of $3.16\times10^6$ cells/mL. Thereto were added influenza virus A/New Caledonia strain (m.o.i. 0.001) and trypsin (DIFCO, Trypsin 250) at various concentrations and the cells were cultured with a 250 mL shaker flask under culture conditions of 100 rpm, 34° C., 5% $CO_2$. A viral amount was measured by ELISA using an anti-HA antibody. Namely, each 100 μL of the culture solution was added to a 98-well ELISA plate (Nunc) coated with a solution of an anti-HA antibody and the plate was left to stand at 37° C. for 1 hour. After washing with PBS, 100 μL of an anti-HA antibody labeled with HRP was added to the plate for reaction at 37° C. for 1 hour. Then, 100 μL of a developing solution was added to the plate and the plate was left to stand at 37° C. for 10 minutes. Measurement was made at a wave length of 450 nm with a microplate reader (BIO-TEK). For control (or calibration curve), purified viruses were used and a viral amount was calculated from absorbance. The results are shown in Table 1. A viral amount in a culture medium was the highest with a trypsin (DIFCO, Trypsin 250) level from 0.9 to 2.7 Tryp.U/mL. In the table, the viral amount is shown in μg/mL and ND means no measurement.

TABLE 1

| Days of culture | Trypsin content | | | |
|---|---|---|---|---|
| | 0.23 U/mL | 0.9 U/mL | 1.8 U/mL | 2.7 U/mL |
| Day 1 | 0 | 0 | 0 | 0 |
| Day 2 | 7.31 | 25.3 | 15.4 | 16.7 |
| Day 3 | 12.7 | 60.0 | 70.0 | 50.0 |
| Day 4 | ND | 113.8 | 135.0 | 91.4 |

(2) High Density Culture of B/Shanghai Strain

High density culture of influenza virus B/Shanghai strain (m.o.i. 0.001) was carried out. The procedures of Example 1-(1) were repeated except that the initial trypsin contents were changed and an initial cell density of $3.83 \times 10^6$ cells/mL was used. The results are shown in Table 2. A viral amount in a culture medium was the highest with a trypsin level from 0.45 to 1.8 Tryp.U/mL. In the table, the viral amount is shown in μg/mL and ND means no measurement.

TABLE 2

| Days of culture | Trypsin content | | | |
|---|---|---|---|---|
| | 0.23 U/mL | 0.45 U/mL | 0.9 U/mL | 1.8 U/mL |
| Day 1 | ND | 0 | 0 | 0 |
| Day 2 | ND | 1.9 | 40.4 | 27.6 |
| Day 3 | 3.3 | 24.6 | 43.7 | 25.1 |
| Day 4 | 5.5 | 35.9 | 35.7 | 23.2 |

Example 2

Effect of Rate of Culture Exchange on High Density Culture of A/New Caledonia Strain MDCK cells after suspension culture in T7m medium (JRH) were centrifuged at a low speed (2000 rpm×3 min.) to separate precipitated cells from culture supernatant. The culture supernatant was adequately mixed with a fresh T7m medium and the mixture was added to the precipitated cells to prepare a solution of cell suspension at an initial cell density of $4.21 \times 10^6$ cells/mL. To 50 mL of this solution of cell suspension was added a trypsin solution at a final concentration of 1.8 Tryp.U/mL. The conditions in Example 1-(1) were used to culture virus-infected cells and a viral amount in culture was measured. The results are shown in Table 3. At 75% exchange of fresh T7m culture, a viral amount reached a plateau and, at a higher rate of culture exchange, remained at the same level. In the table, the viral amount is shown in μg/mL and ND means no measurement.

TABLE 3

| Days of culture | Rate of culture exchange | | | |
|---|---|---|---|---|
| | 0% | 50% | 75% | 100% |
| Day 1 | 0 | 0 | 0 | 0 |
| Day 2 | 0 | 8.4 | 17.0 | 23.5 |
| Day 3 | 0 | 16.7 | 34.0 | 47.0 |
| Day 4 | 1.2 | 36.2 | 55.4 | 59.3 |

Example 3

Effect of Cell Density on High Density Culture of A/New Caledonia Strain

MDCK cells after suspension culture in T7m medium (JRH) were centrifuged at a low speed (2000 rpm×3 min.) and precipitated cells were suspended in 50 mL of a fresh T7m medium at an initial cell density of $3-11 \times 10^6$ cells/mL. To the suspension were added influenza virus A/New Caledonia strain (m.o.i. 0.001) and 1.8 Tryp.U/mL of trypsin (DIFCO, Trypsin 250) for culture. Culture was carried out under the same conditions as in Example 1-(1). As a result, a viral amount in culture increased depending on a cell concentration within a range of a cell density of $3-7 \times 10^6$ cells/mL and thereafter reached a plateau (FIG. 1).

Example 4

Figure 2:
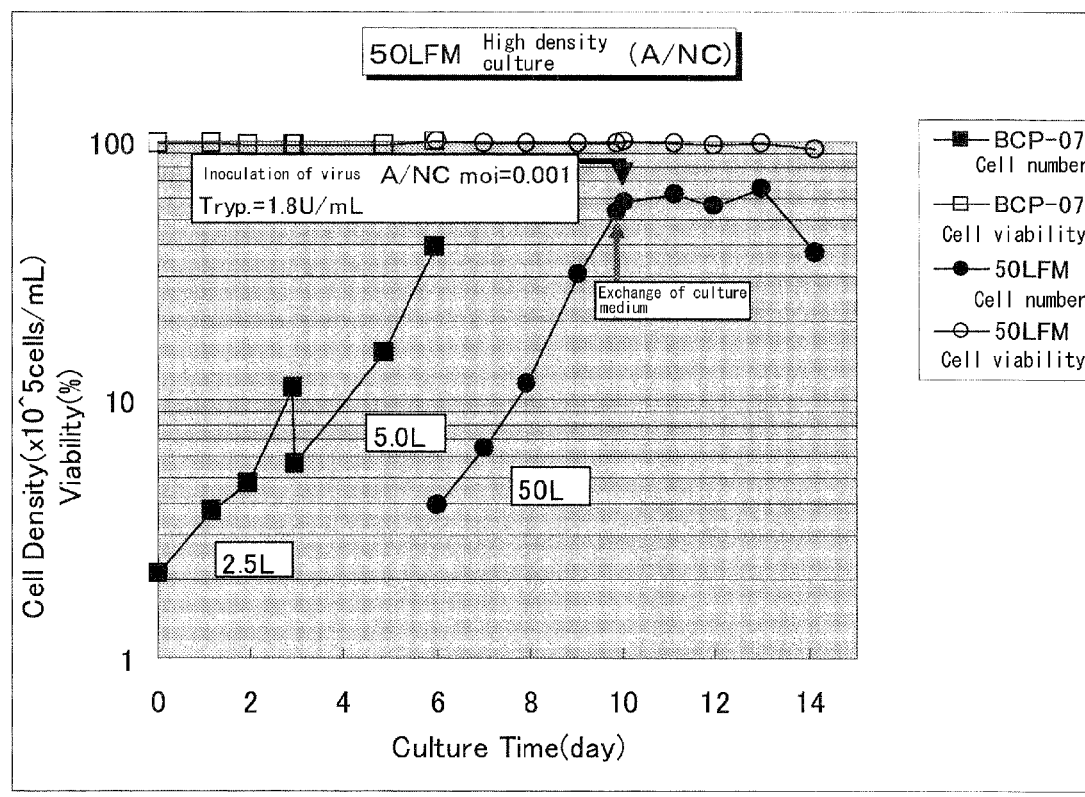
FIG. 2 is a graph showing a culture profile obtained when A/New Caledonia strain is subjected to a large scale culture with a 50 L fermenter.

A Large Scale Production of Influenza Virus in High Density Culture after Culture Medium Exchange MDCK cells after suspension culture in EX-CELL293 medium (JRH) using a 50 L/50 L fermenter were subjected to membrane filtration to aseptically remove culture supernatant. To the resulting cells was added a fresh EX-CELL293 medium at 75% of a rate of culture exchange. An initial cell density became $5.9 \times 10^6$ cells/mL. Thereto were added influenza virus A/New Caledonia strain (m.o.i. 0.001) and 1.8 Tryp.U/mL of trypsin (Sigma, Trypsin cGMP) for culture in a 50 L/50 L fermenter (FIG. 2). Culture conditions were 50 rpm, 34° C. and 3 ppm $O_2$. At Day 4 after initiation of culture, a viral amount in culture medium was measured as in Example 1. As a result, the viral amount reached as high as 120 μg/mL (production per initial cell density: 20 μg/$10^6$ cells).

Figure 3:
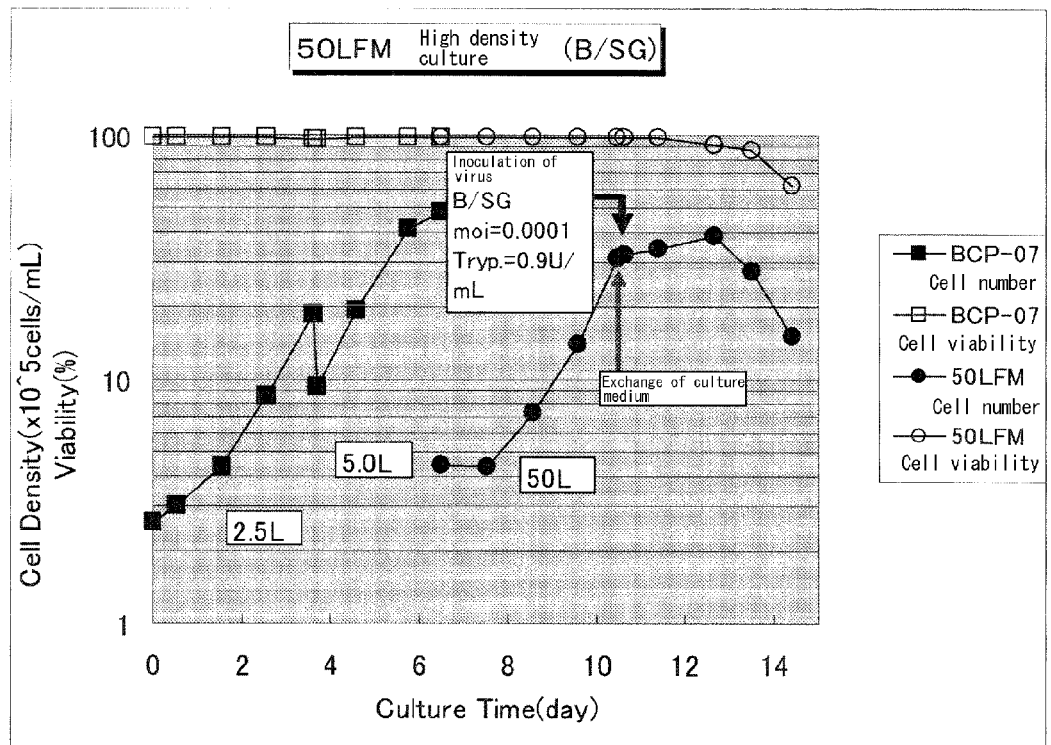
FIG. 3 is a graph showing a culture profile obtained when B/Shanghai strain is subjected to a large scale culture with a 50 L fermenter.

Culture was performed in like manner for B/Shanghai strain and an amount of produced viruses was measured. The same conditions as those for A/New Caledonia strain were used except for an initial cell density of $3.3 \times 10^6$ cells/mL, EX-CELL293 medium and a trypsin concentration of 0.9 Tryp.U/mL (FIG. 3). As a result, the viral amount reached as high as 60 μg/mL (production per initial cell density: 18 μg/$10^6$ cells).

Figure 4:
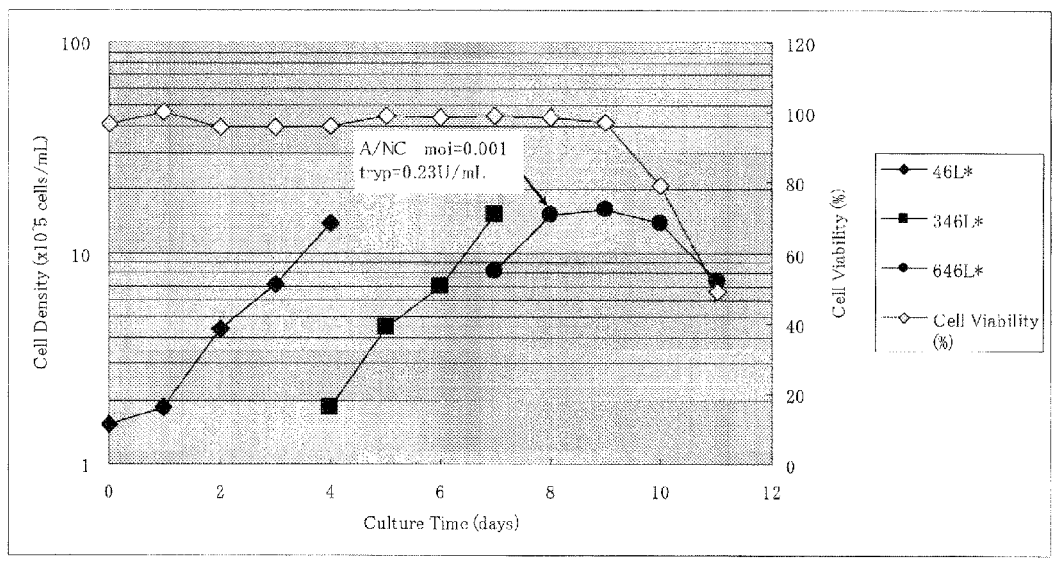
FIG. 4 is a graph showing a culture profile obtained when A/New Caledonia strain is subjected to a large scale culture with a 600 L fermenter.

Effect of Decrease in Inhibitor by Exchange of Culture Medium in A/New Caledonia Strain MDCK cells after suspension culture in M202 medium (JRH) using a 600 L fermenter were diluted two-fold with a fresh M202 medium to an initial cell density of $1.53 \times 10^6$ cells/mL. To 646 L of this cell dilution solution was added a trypsin solution at a final concentration of 0.23 U/mL and further added influenza virus A/New Caledonia strain (m.o.i. 0.001) for culture in a 600 L fermenter under culture conditions: 50 rpm, 34° C. and 3 ppm $O_2$ (FIG. 4). At Day 4 after initiation of culture, a viral amount in culture medium was measured as in Example 1. As a result, the viral amount reached as high as 12.8 μg/mL (production per initial cell density: 8.5 μg/$10^6$ cells).

INDUSTRIAL APPLICABILITY

The method for producing Influenza virus of the present invention may be utilized for obtaining influenza vaccine material at a large scale.

The invention claimed is:

1. A method for propagating influenza virus which comprises:
   (a) culturing influenza virus-sensitive cells selected from the group consisting of MDCK cells, Vero cells, EBx cells, PER.C6 cells and SK-NEP-1 cells in a serum-free medium;
   (b) removing a trypsin inhibitor secreted into the serum-free culture medium of the influenza virus-sensitive cells by washing with a serum-free medium or a buffer; and
   (c) inoculating influenza virus into said influenza virus-sensitive cells and culturing said influenza virus-inoculated cells.

2. The method of claim 1, wherein influenza virus-inoculated cells are cultured in a serum-free medium containing trypsin at 0.45 to 2.7 U/mL.

3. The method of claim 1, wherein said method comprises steps (1) to (5) as follows:
   (1) subjecting a cell culture of influenza virus-sensitive cells in serum-free medium to centrifugation at a low speed or to membrane filtration to isolate cells from the culture supernatant;
   (2) washing the cells with a serum-free medium or a buffer to remove a trypsin inhibitor secreted into the culture of the influenza virus-sensitive cells;
   (3) inoculating influenza virus into the influenza virus-sensitive cells;
   (4) culturing the influenza virus-inoculated cells; and
   (5) adding a trypsin solution at a final concentration of trypsin of 0.45 to 2.7 U/mL while culturing said influenza virus-inoculated cells.

4. The method of claim 1, wherein m.o.i, of influenza virus is 0.0001 to 0.01 and a cell density of said influenza virus-inoculated cells is 3-11×$10^6$ cells/mL.

5. The method of claim 1, wherein said influenza virus-inoculated cells are cultured in suspension culture.

* * * * *

UNITED STATES PATENT AND TRADEMARK OFFICE
CERTIFICATE OF CORRECTION

| | | |
|---|---|---|
| PATENT NO. | : 7,883,844 B2 | |
| APPLICATION NO. | : 12/300625 | |
| DATED | : February 8, 2011 | |
| INVENTOR(S) | : Toshinobu Nouchi et al. | |

It is certified that error appears in the above-identified patent and that said Letters Patent is hereby corrected as shown below:

Title Page;
At section (73) Assignee, correct the incorrect assignee name by delete "JURIDICAL FOUNDATION THE CHEMOSERO-THERAPEUTIC RESEARCH INSTITUTE" and insert
--JURIDICAL FOUNDATION THE CHEMO-SERO-THERAPEUTIC RESEARCH INSTITUTE--.

Signed and Sealed this
Eighteenth Day of October, 2011

David J. Kappos
*Director of the United States Patent and Trademark Office*